(12) United States Patent
Pijnenburg et al.

(10) Patent No.: US 11,364,355 B2
(45) Date of Patent: Jun. 21, 2022

(54) AEROSOL-GENERATING DEVICE AND METHOD FOR USING A SHEET OF AEROSOL-FORMING SUBSTRATE IN AN AEROSOL-GENERATING DEVICE

(71) Applicant: PHILIP MORRIS PRODUCTS S.A., Neuchatel (CH)

(72) Inventors: Johannes Petrus Maria Pijnenburg, Neuchatel (CH); Alexandre Malgat, Neuchatel (CH); Stephane Antony Hedarchet, Lausanne (CH); Noori Moyad Brifcani, Neuchatel (CH); Lucio Maria Rondinara, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 487 days.

(21) Appl. No.: 16/485,627

(22) PCT Filed: Feb. 20, 2018

(86) PCT No.: PCT/EP2018/054090
§ 371 (c)(1),
(2) Date: Aug. 13, 2019

(87) PCT Pub. No.: WO2018/150039
PCT Pub. Date: Aug. 23, 2018

(65) Prior Publication Data
US 2020/0046026 A1   Feb. 13, 2020

(30) Foreign Application Priority Data

Feb. 20, 2017 (EP) .................................... 17156883

(51) Int. Cl.
*A61M 15/06* (2006.01)
*H05B 3/06* (2006.01)
(Continued)

(52) U.S. Cl.
CPC ............. *A61M 15/06* (2013.01); *A24F 40/46* (2020.01); *H05B 3/06* (2013.01); *A24B 15/167* (2016.11); *A24F 40/20* (2020.01)

(58) Field of Classification Search
CPC .......... A61M 15/06; A24F 40/46; H05B 3/06; A24B 15/167
See application file for complete search history.

(56) References Cited

U.S. PATENT DOCUMENTS

| 4,917,128 A | 4/1990 | Clearman |
| 5,074,321 A | 12/1991 | Gentry |

(Continued)

FOREIGN PATENT DOCUMENTS

| CN | 102275418 | 12/2011 |
| CN | 105357991 | 2/2016 |

(Continued)

OTHER PUBLICATIONS

Office Action issued in Russia for Application No. 2019129522 dated Jun. 22, 2021 (4 pages). English translation included.

(Continued)

*Primary Examiner* — Tho D Ta
(74) *Attorney, Agent, or Firm* — Mueting Raasch Group

(57) ABSTRACT

The aerosol-generating device comprises a device housing (2), a mouthpiece (3) associated to the device housing, a receiving chamber (4) configured to receive from external to the device at least a portion of a sheet of aerosol-forming substrate in a non-rolled form and configured to accommodate a cylindrically shaped of aerosol-forming substrate and a holder (6) for holding the sheet of aerosol-forming substrate. The device further comprises a rolling device (7) for receiving a flat or non-rolled sheet of aerosol-forming substrate and for rolling the sheet of aerosol-forming substrate (Continued)

around the holder from the non-rolled form into a cylindrically shaped aerosol-forming substrate.

15 Claims, 3 Drawing Sheets

(51) Int. Cl.
*A24F 40/46* (2020.01)
*A24B 15/167* (2020.01)
*A24F 40/20* (2020.01)

(56) References Cited

U.S. PATENT DOCUMENTS

| | | | | |
|---|---|---|---|---|
| 5,137,034 | A | 8/1992 | Perfetti | |
| 5,261,425 | A | 11/1993 | Raker | |
| 5,271,419 | A | 12/1993 | Arzonico | |
| 5,396,911 | A | 3/1995 | Casey, III | |
| 5,479,948 | A | 1/1996 | Counts | |
| 8,869,792 | B1 | 10/2014 | Lee | |
| 9,999,247 | B2 | 6/2018 | Ruscio | |
| 2014/0305449 | A1 | 10/2014 | Plojoux | |
| 2016/0044963 | A1 | 2/2016 | Saleem | |
| 2016/0044964 | A1 | 2/2016 | Liu | |
| 2016/0120216 | A1 | 5/2016 | Mironov | |
| 2017/0119049 | A1* | 5/2017 | Blandino | A24F 40/46 |

FOREIGN PATENT DOCUMENTS

| | | |
|---|---|---|
| CN | 205667356 | 11/2016 |
| EA | 22838 | 3/2016 |
| EP | 0458526 | 11/1991 |
| EP | 1651296 | 5/2006 |
| EP | 2493342 | 12/2014 |
| JP | H07147965 | 6/1995 |
| JP | 2014534813 | 12/2014 |
| JP | 2016512703 | 5/2016 |
| KR | 20160082262 A * | 7/2016 |
| RU | 2097996 | 12/1997 |
| WO | WO 2015/155289 | 10/2015 |

OTHER PUBLICATIONS

PCT Search Report and Written Opinion for PCT/EP2018/054090 dated Apr. 25, 2018 (13 pages).

Office Action issued in China for Application No. 201880012297.X dated Oct. 28, 2021 (11 pages). English translation included.

Office Action issued in Japan for Application No. 2019-545351 dated Mar. 16, 2022 (5 pages). English translation included.

* cited by examiner

AEROSOL-GENERATING DEVICE AND METHOD FOR USING A SHEET OF AEROSOL-FORMING SUBSTRATE IN AN AEROSOL-GENERATING DEVICE

This application is a U.S. National Stage Application of International Application No. PCT/EP2018/054090 filed Feb. 20, 2018, which was published in English on Aug. 23, 2018, as International Publication No. WO 2018/150039 A1. International Application No. PCT/EP2018/054090 claims priority to European Application No. 17156883.5 filed Feb. 20, 2017.

The invention relates to an aerosol-generating device and a method for using a sheet of aerosol-forming substrate in an aerosol-generating device. In particular, the invention relates to an aerosol-generating device and method wherein a sheet of aerosol-forming substrate is rolled into a cylindrically shaped substrate.

In aerosol-generating devices where a tobacco substrate is heated, the substrate is in the form of a rod made of a sheet of homogenized or reconstituted tobacco material. The sheet is crimped and gathered to form the rod.

It would be desirable to have an aerosol-generating device and method not requiring an elaborate and costly manufacturing process for forming tobacco rods.

According to the invention there is provided an aerosol-generating device. The aerosol-generating device comprises a device housing, a mouthpiece associated to the device housing and a receiving chamber configured to accommodate a cylindrically shaped aerosol-forming substrate. The receiving chamber is also configured to receive from external to the device at least a portion of a sheet of aerosol-forming substrate in a non-rolled form.

The aerosol-generating device further comprises a holder for holding the sheet of aerosol-forming substrate and a rolling device for rolling the sheet of aerosol-forming substrate from the non-rolled form into a cylindrically shaped aerosol-forming substrate.

In the aerosol-generating device according to the invention a sheet of aerosol-forming substrate is in its non-rolled form directly used in and formed by the device into a rod or into a cylindrically shaped substrate.

By the rolling of the sheet of aerosol-forming substrate, the substrate does not need to be crimped for a subsequent gathering. No structuring of the aerosol-forming substrate is required to support a rolling or rod forming, in particular a controlled rod forming. Generally, the rolling of the substrate allows the manufacture of reproducible cylindrically shaped aerosol-forming substrates. In particular, with a given substrate and rolling parameters, a reproducible resistance to draw of the cylindrically shaped substrate may be achieved.

Since the sheet of aerosol-forming substrate is substantially a flat substrate, the substrate may be easy and cost efficient to manufacture. In addition, it may be stacked and stored in a space saving manner. Also an individual packaging is simplified, which may keep the product longer fresh and may reduce damage during transport.

The aerosol-generating device, for example the rolling device, comprises a holder for positioning the sheet of aerosol-forming substrate and for holding the substrate while the substrate is rolled. Holding may be performed by frictional forces, for example holding the substrate against a post or between posts arranged in the device. Preferably, the rolling device or the holder comprises a pair of holding pins. The holding pins of the pair of holding pins are arranged at a distance from each other, thereby defining a passage in between them for insertion of the sheet of aerosol-forming substrate.

Preferably, the sheet is inserted in between the holding pins such as to be arranged symmetrically between the pins. Thus, about equal lengths of the sheet extend to each side of the holding pins.

The sheet of aerosol-forming substrate is rolled around the holder. Preferably, the holder is rotatable. Thereby, the holder itself may be rotatably mounted or may be fixedly mounted on a rotatable base. The rotatable base may, for example, be part of the receiving chamber, for example may form a receiving chamber bottom wall.

Holding pins allow the sheet of aerosol-forming substrate to be rolled around the holding pins. Preferably, the holding pins are rotatable around a common center. Preferably, the pins are mounted on a rotatable base. Preferably, the rotatable base forms a receiving chamber bottom wall. Preferably, the pair of holding pins are fixed relative to the rotatable base, wherein the rotatable base is rotatable relative to a device housing.

Preferably, a holder is integrated into a rolling device.

The receiving chamber may be located within the device housing or within the mouthpiece.

If the receiving chamber is located within the mouthpiece, the mouthpiece may comprise a side wall having two oppositely arranged elongated passages arranged within the side wall. The elongated passages allow insertion of a sheet of aerosol-forming substrate in a non-rolled form therethrough. Preferably a holder is aligned with elongated passages. In particular, a holder in the form of a pair of distanced holding pins or a rolling device comprising a pair of holding pins is preferably arranged such that a passage between the pins is aligned with the elongated passages in the mouthpiece. A pair of pins may also be displaced from a direct alignment with elongated passages. Such a displacement may enhance a hold of the sheet in the holder and may further prevent a slipping of the sheet away or out of the holder. Advantageously, a sheet of aerosol-forming substrate provides stability and flexibility to allow for such an insertion and handling of the sheet.

Preferably, the rolling device of the aerosol-generating device is arranged such that a rotational axis of the sheet of aerosol-forming substrate being wound around the holder is arranged parallel to a longitudinal axis of a receiving chamber of the device. More preferably, the rotational axis of the sheet of aerosol-forming substrate corresponds to a longitudinal axis of the receiving chamber.

Preferably, the rotational axis of the sheet of aerosol-forming substrate is arranged parallel to a longitudinal axis of the rolling device. More preferably, the rotational axis of the sheet of substrate corresponds to a rotational axis of the rolling device.

Preferably, the rotational axis of the sheet of aerosol-forming substrate is arranged parallel to a longitudinal axis of the aerosol-generating device. More preferably, the rotational axis of the sheet of substrate corresponds to longitudinal axis of the aerosol-generating device.

Preferably, a rotational axis of the sheet of substrate corresponds to a rotational axis or to a longitudinal axis of the holder. As such, preferably, a longitudinal axis of the holder is arranged parallel or corresponds to the longitudinal axis of the receiving chamber.

Preferably, the receiving chamber has a shape of a cylinder. A rotational axis of the cylindrically shaped aerosol-forming substrate is then preferably arranged parallel to the longitudinal axis of the cylindrically shaped receiving chamber. More preferably the rotational axis of the cylindrically shaped aerosol-forming substrate corresponds to the longitudinal axis of the cylindrically shaped receiving chamber.

The device comprises a heater for heating the cylindrically shaped aerosol-forming substrate. Preferably, a heater is a resistive or inductive heater.

A heater may be arranged in the mouthpiece or in the device housing. Preferably, the heater is provided in the device housing, for example in device housing walls.

A heater may be integrated into the rolling device. A heater may be integrated into a holder, in particular into a holding pin. A heater may be integrated into both, the rolling device and the holder.

A heater may be integrated into a rotatable base of the rolling device.

A heater may comprise a first heating element integrated into a holding pin or a second heating element integrated into a rotatable base of the rolling device. A heater may comprise both, a first heating element integrated into a holding pin and a second heating element integrated into a rotatable base of the rolling device.

A heating element integrated into a holder allows heating of the cylindrically shaped aerosol-forming substrate from the inside or from a center of the substrate.

A heating element integrated, for example in device housing walls allows heating of the cylindrically shaped aerosol-forming substrate along the circumference of the cylindrically shaped aerosol-forming substrate. Depending on how a heater is integrated into a rotatable base of the rolling device, circumferential heating of a rolled substrate is possible.

For example, in embodiments wherein a second heating element is integrated into a rotatable base of the rolling device, the second heating element may be arranged in a reversibly movable manner. For example, the second heating element may be reversibly movable between a retracted position where the second heating element is inserted into the device housing and an operative position where the second heating element extends from the device housing into the receiving chamber. In the operative position the second heating element is arranged such as to at least partially surround the cylindrically shaped aerosol-forming substrate when said substrate is arranged in the receiving chamber. The second heating element may form a portion of the receiving chamber wall.

Preferably, when the second heating element is in the operative position, the second heating element is arranged in correspondence with elongated passages of a mouthpiece thereby closing the elongated passages. Thereby, the receiving chamber otherwise open through the elongated passages of the mouthpiece is closed by the second heating element.

Preferably, the second heating element comprises two heating portions arranged at opposite sides of the receiving chamber. Preferably, the two heating portions form curved parts of the receiving chamber side wall.

Preferably, the mouthpiece is detachable from the device housing. For example, the mouthpiece may entirely or partly be detachable from the device housing. The mouthpiece may, for example, be hingedly connected to the device housing.

Preferably, the mouthpiece is removably connectable to the device housing.

Preferably, the mouthpiece is connectable to a rolling device arranged in a device housing.

The device may comprise a connector. The connector comprises an open coupling, where the rolling device is rotatable with respect to the device housing. The connector comprises a locked coupling where rotation of the rolling device relative to the device housing is prevented.

For example, a connector of a mouthpiece and a rolling device may comprise an open coupling where the mouthpiece and the rolling device are engaged and rotatable with respect to the device housing. The mouthpiece and rolling device may comprise a locked coupling where the mouthpiece and the rolling device are engaged and rotation relative to the device housing is prevented.

Alternatively or in addition, rolling device and device housing may comprise a connector. In an open coupling the device housing and the rolling device are not engaged and the rolling device is rotatable with respect to the device housing. In a locked coupling, the device housing and the rolling device are engaged and the rolling device is not rotatable with respect to the device housing.

Open and locked coupling may define the device as being in a rolling status of the device and in a use status of the device. Preferably, use of the device, such as heating and aerosol generation, is prevented when mouthpiece and rolling device or when device housing and rolling device are in the open coupling. Preferably, rolling or rotation of the rolling device and possibly also the mouthpiece is prevented when the rolling device and the device housing or when the mouthpiece and the rolling device are in the locked coupling. The coupling may be connected to a control of the device and prevent or allow heating of a rolled-up substrate in the device.

The aerosol-generating device is a hand-held device. Preferably, the device has an elongate shape. Preferably, the device has the shape of a pen.

According to the invention, there is also provided a method for using a sheet of aerosol-forming substrate in an aerosol-generating device. The method comprises the step of providing an aerosol-generating device comprising a receiving chamber for accommodating a cylindrically shaped aerosol-forming substrate. The method further comprises the steps of providing a sheet of aerosol-forming substrate and arranging at least a portion of the sheet of aerosol-forming substrate in the receiving chamber. Yet a further step of the method comprises rolling the sheet of aerosol-forming substrate into a cylindrically shaped aerosol-forming substrate in the receiving chamber.

The device comprises a rolling device and the at least a portion of the sheet of aerosol-forming substrate is arranged at the rolling device in the receiving chamber.

The method may further comprise the step of positioning the sheet of aerosol-forming substrate in between two holding pins arranged in the receiving chamber. The sheet is then rolled around the two holding pins to the cylindrical shape. The holding pins are arranged at a distance such as to allow insertion and positioning of the sheet between the holding pins.

Preferably, in the method according to the invention the step of rolling the sheet of aerosol-forming substrate comprises the step of rotating parts of the device relative to the device housing or rotating the sheet of aerosol-forming substrate relative to the device housing. The method may comprise both, rotating parts of the device relative to the device housing and rotating the sheet of aerosol-forming substrate relative to the device housing.

Preferably, rotating parts of the device comprises rotating parts of the receiving chamber.

For example, a holder such as two holding pins may be rotated or a base preferably comprising the holder such as the two holding pins, may be rolled.

Preferably, the method comprises the step of heating the cylindrically shaped aerosol-forming substrate. Heating is preferably done by heating portions of the receiving chamber, for example heating receiving chamber walls, or by heating a holder, for example holding pins, around which the substrate is rolled. However, heating may also be performed by directly heating the aerosol-forming substrate, for example by inductively heating susceptor material arranged in the sheet of aerosol-forming substrate.

Preferably, the sheet of aerosol-forming substrate is a flat substrate having a flexibility sufficient to be arranged in the device according to the invention and to be rolled into a circumferential shape.

The term 'flat' substrate is used herein to refer to a substrate that is in the form of a substantially two dimensional topological manifold. Thus, the flat substrate extends in two dimensions along a surface substantially more than in a third dimension. In particular, the dimensions of the flat substrate in the two dimensions within the surface is at least 5 times larger than in the third dimension, normal to the surface. Preferably, the flat substrate is planar.

A sheet of aerosol-forming substrate may have a thickness in a range between 0.2 millimeter and 6 millimeter, preferably, between 0.5 millimeter and 4 millimeter, for example between 0.2 millimeter and 2 millimeter or between 0.4 millimeter and 4 millimeter.

Throughout this application, whenever a value is mentioned, this is to be understood such that the value is explicitly disclosed. However, a value is also to be understood as not having to be exactly the particular value due to technical considerations.

The sheet of aerosol-forming substrate in the circumferential shape may have a diameter in a range between 4 millimeter and 18 millimeter, preferably, between 6 millimeter and 12 millimeter, for example between 7 millimeter and 10 millimeter.

The aerosol-forming substrate comprises a flexibility such as to be rolled into the cylindrical shape. Preferably, the substrate comprises a flexibility such as to not break or be ruptured upon rolling. Preferably, rolling excludes a folding of the substrate onto itself. Preferably, the substrate is not bent by more than 135 degrees upon rolling, more preferably by not more than 90 degree upon being rolled by the rolling device.

Preferably, the sheet of aerosol-forming substrate is a single sheet of aerosol-forming substrate.

The aerosol-forming substrate may comprise a tobacco-containing material containing volatile tobacco flavour compounds, which are released from the substrate upon heating. Alternatively, the aerosol-forming substrate may comprise a non-tobacco material. The aerosol-forming substrate may further comprise an aerosol former. Examples of suitable aerosol formers are glycerine and propylene glycol.

The aerosol-forming substrate may comprise, for example, reconstituted tobacco, homogenised tobacco, extruded tobacco and expanded tobacco.

Optionally, the aerosol-forming substrate may contain additional tobacco or non-tobacco volatile flavour compounds, to be released upon heating of the aerosol-forming substrate. The aerosol-forming substrate may also contain micro-capsules that, for example, include the additional tobacco or non-tobacco volatile flavour compounds and such micro-capsules may melt during heating of the solid aerosol-forming substrate.

The aerosol-forming substrate may be a sheet of homogenised tobacco material that has been formed or cut into a desired shape and size.

Preferably, the sheet of aerosol-forming substrate is substantially rectangular.

A tobacco containing aerosol-forming substrate comprises tobacco particles, fiber particles, aerosol former, binder and for example also flavours.

Preferably, the aerosol-forming tobacco substrate is a tobacco sheet comprising tobacco material, fibers, binder and aerosol former. Preferably, the tobacco sheet is a cast leaf. Cast leaf is a form of reconstituted tobacco that is formed from a slurry including tobacco particles, fiber particles, aerosol former, binder and for example also flavours.

One or more aerosol former may be combined to take advantage of one or more properties of the combined aerosol formers. For example, triacetin may be combined with glycerol and water to take advantage of the triacetin's ability to convey active components and the humectant properties of the glycerol.

The aerosol-forming substrate may contain waxes or fats, which waxes or fats are added for a low temperature release of aerosol-forming substances from the solid aerosol-forming substrate. Some waxes and fats are known for their ability to lower the temperature where an aerosol former is released from a solid substrate containing said waxes or fats.

The sheet of aerosol-forming substrate may be a sheet of cellulose material impregnated with nicotine, preferably comprising one or more flavours.

Preferably, the sheet of aerosol-forming substrate is a sheet of homogenised tobacco material comprising one or more aerosol-formers.

The invention is further described with regard to embodiments, which are illustrated by means of the following drawings, wherein.

Figure 1:
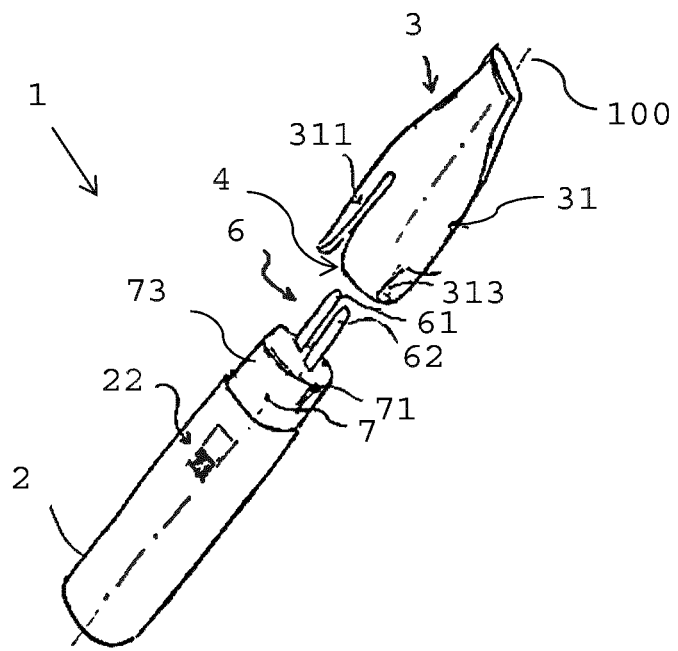
FIG. 1 shows an aerosol-generating device.

FIG. 1 shows an aerosol-generating device in the shape of a pen comprising a device housing 2 and a mouthpiece 3. In the device housing 2 a battery and a control unit may be located (not shown). The mouthpiece 3 is detachable from and reversibly connectable to the device housing 2.

The mouthpiece 3 comprises a cavity 4 for receiving a rolled-up or cylindrically shaped sheet of aerosol-forming (not shown in FIG. 1).

The device 1 also comprises a rolling apparatus 7 arranged in the device housing 2. The rolling apparatus 7 is configured to confer a rolled configuration to the sheet of aerosol-forming substrate. In the example shown in FIG. 1, the rolling apparatus 7 is rotatably connected to the device housing 2. More specifically, the rotatable base 73 of the rolling apparatus 7 may rotate about an axis 100 of the device 1. A holder for holding the sheet of aerosol-forming substrate is embodied as winding element 6. The winding element 6 is mounted integral to the rotatable base 73 and includes in this example a couple of distanced protruding pins 61, 62. The pins 61,62 are mutually arranged defining there-between a passage for insertion of the sheet of substrate 5.

The device 1 further comprises a heating arrangement adapted to cooperate with the substrate when in the rolled configuration such as to generate inhalable aerosol.

The heating arrangement may comprise a first inner heating element arranged on the protruding pins 61, 62 such as to physically contact the rolled-up substrate.

Alternatively or additionally, a heating arrangement may comprise a second outer heating element mounted on the rotatable base 7, for example as shown further below.

Figure 2:
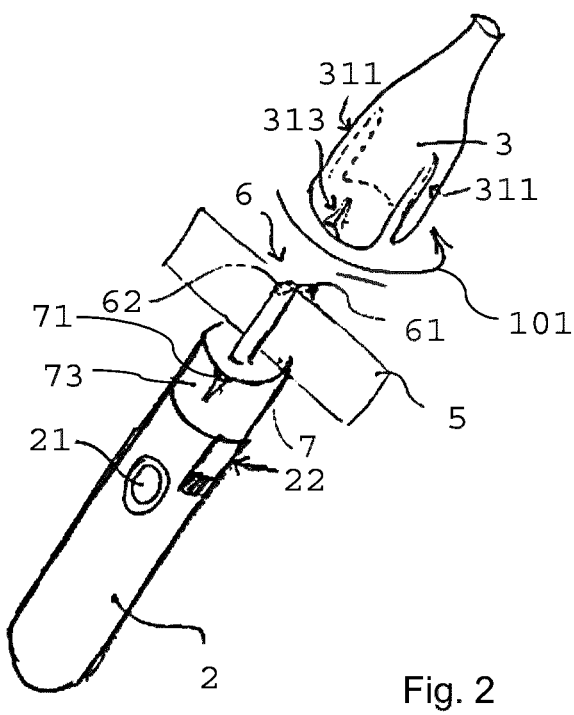
FIG. 2 shows the aerosol-generating device of FIG. 1 comprising a sheet of aerosol-forming substrate.

As illustrated in FIG. 2 the sheet of substrate 5 in its non-rolled form is inserted between the protruding pins 61, 62.

The rotatable base 73 comprises two oppositely arranged projection guides 71. The projection guides 71 are adapted to be inserted into corresponding receiving grooves 313 located along an edge of a side wall 31 of the detachable mouthpiece 3.

The mouthpiece 3 defines along its sidewall 31 two opposed and distally open elongated vertical passages 311. By this, the mouthpiece 3 can be positioned on the rotatable base 7 of the device housing 2 with the unrolled substrate 5 passing through the vertical passages 311 of the mouthpiece.

A connection is established between the mouthpiece 3 and the rotatable base 7 by means of cooperation of the projection guides 71 and corresponding receiving grooves 313.

Once a connection between mouthpiece 3 and rotatable base 7 has been established, the user can, for example manually, rotate the mouthpiece 3 as indicated with arrow 101. This will result in a rotation of the rotatable base 7 with respect to the device housing 2 and consequently a rotation of the winding element 6. The rotation of the pins 61, 62 of the winding element 6 will then cause the rolling of the substrate 5 around the pins 61,62.

A manually slidable switch 22 is arranged in the device housing. As may be seen in FIG. 1 and FIG. 2, the switch is in the down position. The switch 22 is connected to an outer heating element (not shown), which is in the retracted position inside the device housing 2 in FIGS. 1 and 2. In the retracted position the outer heating element allows for insertion of the substrate 5 between the protruding pins 61, 62 as may be seen in FIG. 2.

The outer heating element is movable from the retracted position, where it is inserted into the device housing 2 and an operative position where it protrudes out of the device housing 2. The outer heating element is movable by means of the switch 22 as shown in FIG. 3.

Figure 3:
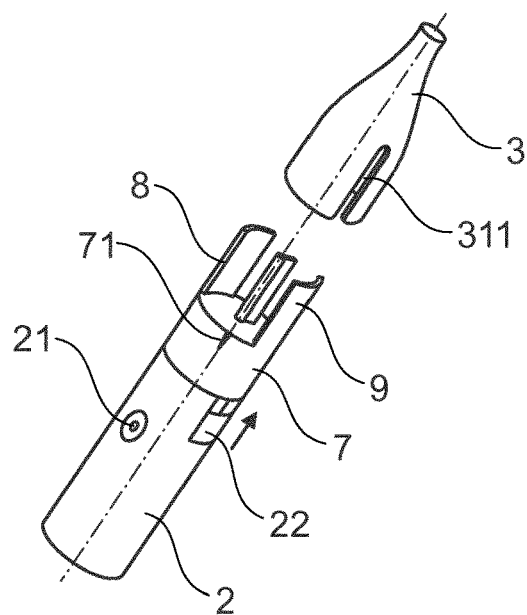
FIG. 3 illustrates an aerosol-generating device comprising movable heating elements in operative position.

FIG. 3 is a perspective view of the device 1, where the outer heating element is in the operative, extracted position. Accordingly switch 22 is in the up position.

The outer heating element includes two opposed curved heating plates 8, 9. Advantageously, heating plates 8, 9 when in the operative position are located in correspondence to the elongated vertical passages 311 of the mouthpiece 3. Thereby, the cavity 4 where the substrate is located in is closed thus improving the heating process.

Alternatively, the outer heating element may also include a single circumferential plate, adapted to encircle a rolled substrate 5 and heat it to generate inhalable aerosol.

In FIG. 3 the mouthpiece 3 is drawn detached from the device housing 2 for better view onto the outer heating element in the operative position.

Figure 4:
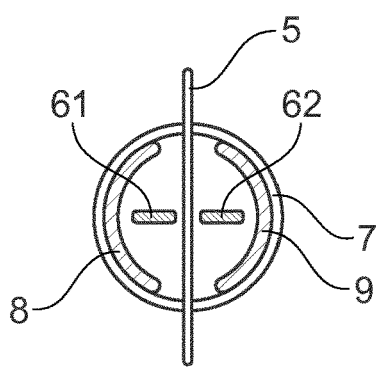
FIG. 4 shows a sheet of aerosol-forming substrate arranged in the device.

FIG. 4 is a top view of the device 1 showing the rotatable base 7 including protruding pins 61, 62, the unrolled sheet of substrate 5 located between the pins and the heating plates 8, 9 of the outer heating element with the heating plates 8,9 in the retracted position.

Figure 5:
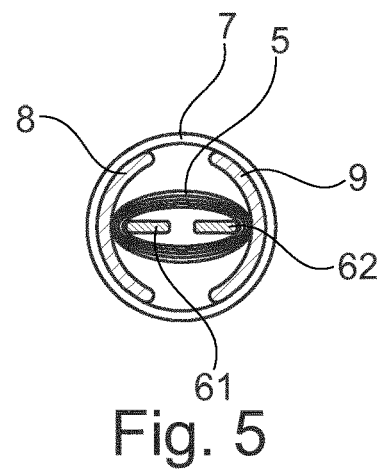
FIG. 5 shows the sheet of aerosol-forming substrate after rolling into a cylindrical shape.

FIG. 5 shows the device 1 in a top view where the sheet of substrate 5 has been wound around pins 61, 62 and the heating plates 8,9 are in the operative position. The rolled sheet is in close contact with the heating plates 8,9.

Figures 6, 7:
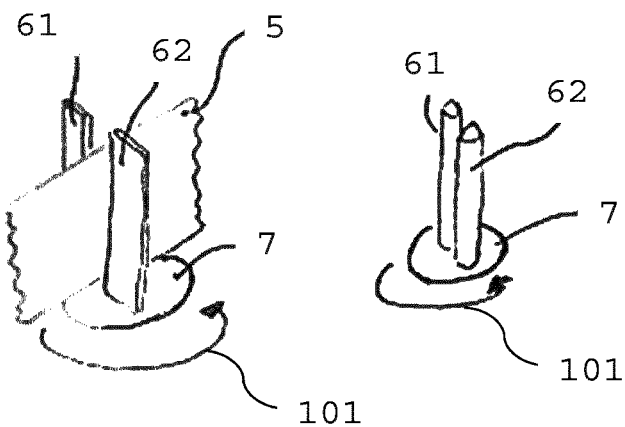
FIG. 6, 7 are schematic illustrations of the rolling apparatus with different embodiments of holding pins.

FIG. 6 and FIG. 7 show perspective views of protruding pins having rectangular cross sections and having circular cross sections. The further distanced pins of FIG. 6 simplify the insertion of the unrolled sheet of substrate 5 between the pins 61,62. A more narrow arrangement of the pins as shown in FIG. 7 may support a holding of the sheet once inserted between the pins 61,62.

The pins 61,62 are mounted on a rotatable base 7 and may rotate anti-clockwise in the direction of arrow 101.

Figure 8:
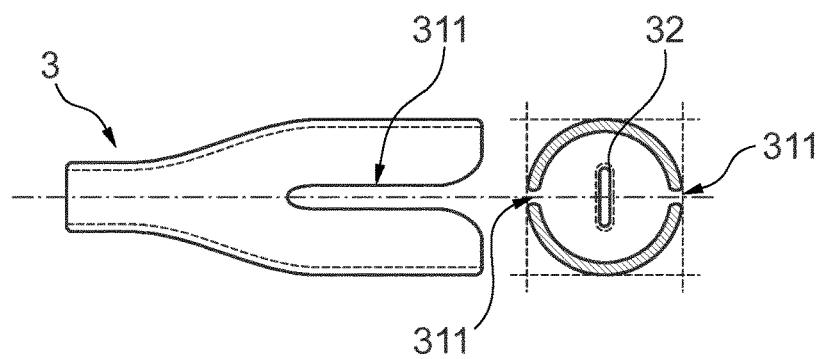
FIG. 8 shows a mouthpiece in a side view and a cross sectional view.

FIG. 8 shows the mouthpiece 3 in a side view and a bottom view. The bottom view allows view onto the outlet 32 of the mouthpiece 3. The mouthpiece has a circular cross section with a narrowing portion versus the outlet 32. In the embodiment of FIG. 8, the opposite arranged vertical passages 311 extend along about half of the length of the mouthpiece.

Figures 9, 10:
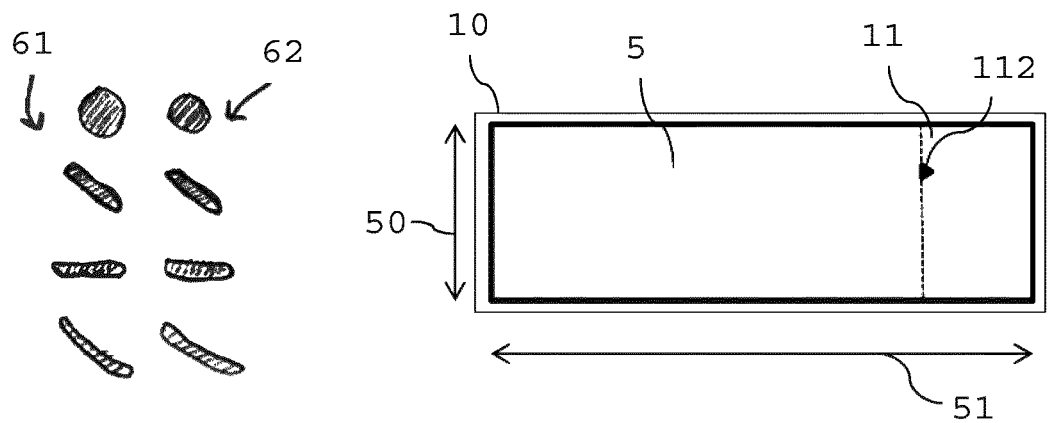
FIG. 9 shows different embodiments of holding pins.
FIG. 10 shows a sheet of aerosol-forming substrate.

FIG. 9 shows different examples of shapes of protruding pins 61, 62 of the winding element 6. In particular, pins 61, may have a circular or rectangular cross-section. Pins having a rectangular cross section may be straight or may have a slightly curved shape as shown in the bottommost example shown in FIG. 9. Pins 61,62 having a rectangular cross section may be arranged in parallel or may be aligned in one line.

FIG. 10 shows a sheet of aerosol-forming substrate 5. In this flat unrolled form, the substrate may be inserted into the device 1. Preferably, the sheet 5 is made of reconstituted cast leaf tobacco.

The substrate 5 has a height 50 and a length 51 configured to be used with the device 1. In a non-limiting example, the size of the sheet 5 is 12 millimeter times 125 millimeter. The size may, for example, be adapted to the size, for example a diameter, of a desired rolled-up sheet, the size of the cavity 4 in a device 1 or a desired amount of aerosol to be generated.

To limit direct contact of a user with the tobacco substrate 5, the substrate 5 may be provided with an envelope material 10. Preferably, the envelope material 10 is made of paper.

The envelope material 10 comprises an opening portion 11, for the extraction of the substrate 5 from the envelope material. Opening portion 11 comprises a tear line having a tab 112 for facilitating opening of the envelope.

The opening portion 11 is located in proximity of a longitudinal edge of the envelope material 10. A user may tear the paper envelope 10 along the tearing line 11 by the aid of the tab 112. While holding the rectangular envelope by the short opening portion 11, the long portion of the envelope may be removed.

By holding the short portion of the envelope a user can position the substrate 5 or a portion of the substrate, between the pins 61,62 of a winding element 6 and then proceeding with the winding as explained above. In this way, the substrate 5 can be inserted into the cavity 5 and rolled without the need to be touched by the user.

Figures 11, 12:
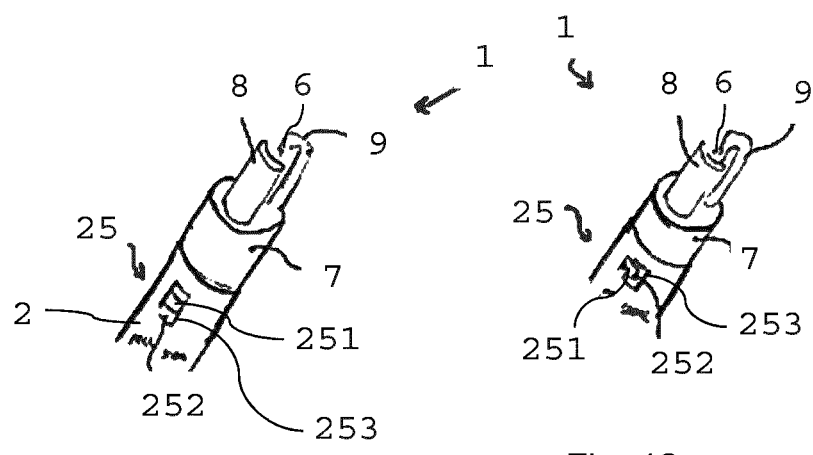
FIG. 11,12 illustrates a connector between a rolling device and a device housing.

In FIG. 11 and FIG. 12, a rotatable base 7 and housing 2 are engageable by a connector 25.

The rotatable part 7 comprises a tab 251 which may extend outwards through a side opening 253 in the housing 2 as shown in FIG. 12. Thereby housing and rotatable base 7 are engaged and rotation of the base 7 relative to the housing is prevented. In the non-extending position of the tab 251 as shown in FIG. 11, rotatable base 7 and housing 2 are not engaged. In this position, base 7 may rotate relative to the housing 2.

Housing 2 comprises a switch 252 manually movable between a "smoke" position and a "roll" position.

When the switch 252 is set in the roll position (FIG. 11), tab 251 is prevented from protruding outwards. Thus, engagement with the housing 2 is not possible. In this way, the rotatable base 7 can freely rotate with respect to the housing 2 until a substrate 5 is wound around the winding element 6.

When the switch 252 is set in the "smoke" position, (FIG. 12), tab 251 extends outwards from the housing when in correspondence with the side opening 253. Thus, a connection between rotatable base 7 and housing 2 is established, which prevents further relative rotation between base 7 and housing 2. In the smoke position, a user may start an inhaling experience. For example, a user may activate a start button 21 as shown in FIG. 2 to initiate heating of the substrate.

The invention claimed is:

1. Aerosol-generating device comprising a device housing,
a mouthpiece associated to the device housing;
a receiving chamber configured to receive from external to the device at least a portion of a sheet of aerosol-forming substrate in a non-rolled form and configured to accommodate a cylindrically shaped aerosol-forming substrate;
a holder for holding the sheet of aerosol-forming substrate, and
a rolling device for rolling the sheet of aerosol-forming substrate around the holder into the cylindrically shaped aerosol-forming substrate.

2. Device according to claim 1, wherein the holder comprises a pair of holding pins, which holding pins are arranged at a distance from each other, thereby defining a passage in between them for insertion of the sheet of aerosol-forming substrate.

3. Device according to claim 2, wherein the pair of holding pins are fixed relative to a rotatable base, which rotatable base is rotatable relative to the device housing.

4. Device according to claim 1, wherein the receiving chamber is located within the mouthpiece, and wherein the mouthpiece comprises a side wall having two oppositely arranged elongated passages for insertion there-through of the sheet of aerosol-forming substrate.

5. Device according to claim 4, comprising a heater for heating the cylindrically shaped aerosol-forming substrate.

6. Device according to claim 5, wherein the heater is integrated into the rolling device or the holder or integrated into both the rolling device and the holder.

7. Device according to claim 5, wherein the heater comprises a first heating element integrated into a holding pin or a second heating element integrated into a rotatable base of the rolling device or comprises a first heating element integrated into a holding pin and a second heating element integrated into a rotatable base of the rolling device.

8. Device according to claim 7, wherein the second heating element is reversibly movable between a retracted position where the second heating element is inserted into the device housing and an operative position where the second heating element extends from the device housing into the receiving chamber.

9. Device according to claim 8, wherein the second heating element when in the operative position is arranged in correspondence with the elongated passages of the mouthpiece thereby closing the elongated passages.

10. Device according to claim 1, comprising a connector comprising an open coupling where the rolling device is rotatable with respect to the device housing, and a locked coupling where rotation of the rolling device relative to the device housing is prevented.

11. Method for using a sheet of aerosol-forming substrate in an aerosol-generating device, the method comprising the steps of:
providing an aerosol-generating device comprising a receiving chamber for
accommodating a cylindrically shaped aerosol-forming substrate;
providing a sheet of aerosol-forming substrate; arranging at least a portion of the sheet of aerosol-forming substrate in the receiving chamber; and
rolling the sheet of aerosol-forming substrate into the cylindrically shaped aerosol-forming substrate in the receiving chamber.

12. Method according to claim 11, comprising the step of positioning the sheet of aerosol-forming substrate in between two holding pins arranged in the receiving chamber.

13. Method according to claim 11, wherein the step of rolling the sheet of aerosol-forming substrate comprises the step of rotating parts of the device relative to the device housing or rotating the sheet of aerosol-forming substrate relative to the device housing, or by both rotating parts of the device relative to the device housing and rotating the sheet of aerosol-forming substrate relative to the device housing.

14. Method according to claim 11, comprising the step of heating the cylindrically shaped aerosol-forming substrate.

15. Method according to claim 11, wherein the sheet of aerosol-forming substrate is a sheet of homogenised tobacco material comprising one or more aerosol-formers.

* * * * *